US009684162B2

(12) United States Patent
Whitcomb et al.

(10) Patent No.: US 9,684,162 B2
(45) Date of Patent: Jun. 20, 2017

(54) OPTICAL SENSORS

(71) Applicant: Goodrich Corporation, Charlotte, NC (US)

(72) Inventors: Kevin J. Whitcomb, Shrewsbury, MA (US); Robert Basedow, Tea Tree Gully (AU)

(73) Assignee: Goodrich Corporation, Charlotte, NC (US)

( * ) Notice: Subject to any disclaimer, the term of this patent is extended or adjusted under 35 U.S.C. 154(b) by 0 days.

(21) Appl. No.: 15/090,916

(22) Filed: Apr. 5, 2016

(65) Prior Publication Data

US 2016/0299333 A1 Oct. 13, 2016

Related U.S. Application Data

(60) Provisional application No. 62/145,291, filed on Apr. 9, 2015.

(51) Int. Cl.
*G02B 26/00* (2006.01)
*G02B 7/00* (2006.01)
(Continued)

(52) U.S. Cl.
CPC .......... *G02B 26/007* (2013.01); *G01J 3/0202* (2013.01); *G01J 3/26* (2013.01);
(Continued)

(58) Field of Classification Search
CPC .... G02B 7/008; G02B 7/1822; G02B 26/007; G01N 21/00; G01N 21/01; G01N 2021/0106; G01N 2021/0112; G01J 1/00; G01J 1/42; G01J 3/0202; G01J 3/0213; G01J 3/26; G01J 3/28; G01J 3/2803;
(Continued)

(56) References Cited

U.S. PATENT DOCUMENTS 2,938,141 A * 5/1960 Garbuny ................ H01J 31/49 250/330
4,227,082 A * 10/1980 Mayeux ................ G01T 1/2921 250/336.1

(Continued)

OTHER PUBLICATIONS

European Search Report from European Patent Office dated Aug. 25, 2016 for Application No. EP16164381.

*Primary Examiner* — Loha Ben
(74) *Attorney, Agent, or Firm* — Locke Lord LLP; Scott D. Wofsy; Alicia J. Carroll

(57) ABSTRACT

An optical sensor includes an array of pixels configured to convert photons into electrons for forming an image. A tunable filter assembly is optically connected to the array of pixels for passing an adjustable bandwidth of photons to the array of pixels. The tunable filter assembly includes a first mirror defining an optical axis and a second mirror spaced apart from the first mirror along the optical axis. A first electrode is mechanically connected to the first mirror and a second electrode is fixed relative to the second mirror. The first and second electrodes are positioned relative to one another to adjust the position of the first mirror with respect to the second mirror when a voltage is applied across the first and second electrodes to tune the spectral bands being passed through the filter assembly to the array of pixels.

10 Claims, 2 Drawing Sheets

100
104
102
111
114b
104
120
118
114
110
116
114a
A
120
111
106
112
108
A

(51) Int. Cl.

| | |
|---|---|
| ***H04N 5/225*** | (2006.01) |
| ***G01J 3/02*** | (2006.01) |
| ***G01J 3/28*** | (2006.01) |
| ***G01J 3/26*** | (2006.01) |
| *G01N 21/01* | (2006.01) |

(52) U.S. Cl.
CPC ........... *G01J 3/2803* (2013.01); *G01J 3/2823* (2013.01); *G02B 7/008* (2013.01); *H04N 5/2254* (2013.01); *G01J 3/28* (2013.01); *G01J 2003/2806* (2013.01); *G01J 2003/2826* (2013.01); *G01N 21/01* (2013.01)

(58) Field of Classification Search
CPC ............. G01J 3/2823; G01J 2003/2806; G01J 2003/2826; H04N 5/2254; H04N 7/144
USPC ................ 359/241, 244, 245, 262, 290–295; 250/330, 333, 336.1, 353, 201.1, 370.1, 250/393, 394, 458.1
See application file for complete search history.

(56) References Cited

U.S. PATENT DOCUMENTS

| | | | | |
|---|---|---|---|---|
| 7,009,680 | B2 * | 3/2006 | Cavanaugh | G02F 1/216 349/18 |
| 7,714,923 | B2 * | 5/2010 | Cok | H04N 7/144 345/175 |
| 7,969,639 | B2 | 6/2011 | McNie et al. | |
| 9,196,781 | B2 * | 11/2015 | Tian | H01L 27/14603 |
| 9,261,998 | B2 * | 2/2016 | Kurokawa | G06F 3/0412 |
| 9,397,477 | B2 * | 7/2016 | Fu | H01S 3/1065 |
| 9,460,886 | B2 * | 10/2016 | Jiang | H01J 29/46 |
| 9,557,856 | B2 * | 1/2017 | Send | G01S 17/46 |
| 2002/0015215 | A1 | 2/2002 | Miles | |
| 2002/0061042 | A1 | 5/2002 | Wang et al. | |
| 2008/0049228 | A1 | 2/2008 | Chan | |
| 2012/0050742 | A1 | 3/2012 | Sano | |
| 2016/0084761 | A1 * | 3/2016 | Rothberg | C12Q 1/6874 506/4 |

* cited by examiner

OPTICAL SENSORS

CROSS REFERENCE TO RELATED APPLICATIONS

This application claims the benefit of and priority to U.S. Provisional Patent Application No. 62/145,291, filed on Apr. 9, 2015, which is incorporated herein by reference in its entirety.

BACKGROUND OF THE INVENTION

1. Field of the Invention

The present disclosure relates to imaging devices, and more particularly to imaging devices for forming multi-chromatic images or for taking multi-spectral measurements.

2. Description of Related Art

Optical sensors can use spectral imaging for remote detection and discrimination of materials of interest. Hyper-spectral imagery can discriminate between materials, but generally requires large pixels or long integration times for sufficient signal strength which limits the effective detection range. For long-range remote detection applications, multi-spectral imagery can be a valuable tool that produces high-resolution imagery, but multispectral imagery has less spectral diversity than hyperspectral imagery, making it more difficult to discriminate between multiple materials.

There is an ever present need in the art for optical sensors with high spectral diversity and ability to discriminate between materials while maintaining or increasing effective detection range, efficiency, and spatial resolution. The present disclosure provides a solution for this need.

SUMMARY OF THE INVENTION

An optical sensor includes an array of pixels configured to convert photons into electrons for forming an image. A tunable filter assembly is optically connected to the array of pixels for passing an adjustable bandwidth of photons to the array of pixels. The tunable filter assembly includes a first mirror defining an optical axis and a second mirror spaced apart from the first mirror along the optical axis. A first electrode is mechanically connected to the first mirror and a second electrode is fixed relative to the second mirror. The first and second electrodes are positioned relative to one another to adjust the position of the first mirror with respect to the second mirror when a voltage is applied across the first and second electrodes to tune the spectral bands being passed through the filter assembly to the array of pixels.

The tunable filter assembly can be one of a plurality of filter assemblies, for example, three filter assemblies, arranged in rows over the array of pixels. Each filter assembly can be optically connected to respective sections of the array of pixels to pass a separate adjustable bandwidth to one of the respective sections to create high-resolution, long-range multi-spectral imagery with tunable spectral bands. The tunable filter assembly can include a plurality of electrical bond pads spaced apart along the array of pixels electrically connected to the first electrode to supply an even voltage to the first electrode. The adjustable bandwidth of the tunable filter assembly can be within at least one of a SWIR, NIR, MWIR, LWIR, or visible band.

The tunable filter assembly can include a frame operatively connected between the first mirror and the first electrode. The first electrode can be connected to a first portion of the frame and the first mirror is connected to a second portion of the frame. The frame can include a plurality of spaced apart bridges connecting between the first and second portions of the frame to suspend the first mirror and the second portion of the frame over the second mirror. The tunable filter assembly can include a plurality of spaced apart posts extending between the first and second electrodes to separate the first electrode apart from the second electrode in a direction parallel to the optical axis. Each of the bridges of the frame can connect between the first and second portions of the frame midway between a respective pair of the posts. The posts can be positioned to allow flexure of the first electrode and the first portion of the frame in a direction parallel to the optical axis when a voltage is applied, thereby adjusting the position of the first mirror along the optical axis and tuning the adjustable bandwidth passing through the tunable filter assembly. The array of pixels and the tunable filter assembly can be cryogenically cooled.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein.

DETAILED DESCRIPTION OF THE PREFERRED EMBODIMENTS

Figure 1:
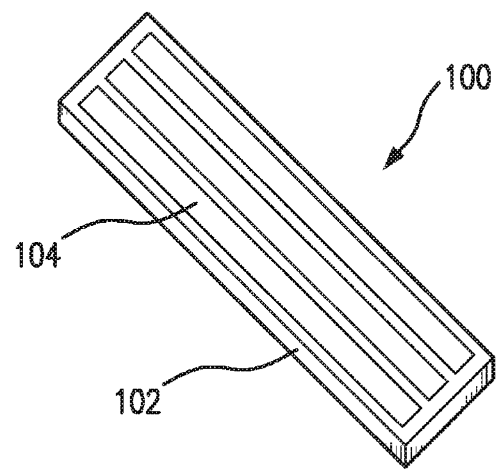
FIG. 1 is a schematic perspective view of an exemplary embodiment of a portion of an optical sensor constructed in accordance with the present disclosure, showing an array of filters in conjunction with an array of pixels.

Reference will now be made to the drawings wherein like reference numerals identify similar structural features or aspects of the subject disclosure. For purposes of explanation and illustration, and not limitation, a partial view of an exemplary embodiment of an optical sensor in accordance with the disclosure is shown in FIG. 1 and is designated generally by reference character 100. Other embodiments of optical sensors in accordance with the disclosure, or aspects thereof, are provided in FIGS. 2-3, as will be described. The systems and methods described herein provide for optical sensors having a multi-spectral imaging system with band pass tuning capabilities resulting in the ability to actively match a band pass with a particular material of interest.

As shown in FIG. 1, an optical sensor 100 includes an array of pixels 102 configured to convert photons into electrons for forming an image. A tunable filter assembly 104 is optically connected to the array of pixels 102 for passing an adjustable bandwidth of photons to array of pixels 102. Tunable filter assembly 104 is one of a plurality of filter assemblies 104, for example, three filter assemblies 104, optically connected to respective sections of array of pixels 102. Each filter assembly 104 is configured to pass a separate adjustable bandwidth to one of the respective sections. It is contemplated that tunable filter assemblies 104 can be applied to closely spaced, line array focal planes, like array 102. It is also contemplated that filter assemblies 104 can be applied to other arrays, such as area array scanners. Traditional tunable filter technologies, e.g. liquid crystal, acoustic optic cells, and the like, are not able to be used in such closely spaced configurations. Those skilled in the art will readily appreciate that filter assemblies 104 can withstand cryogenic temperatures, making them compatible with cooled focal plane technologies, such as those using HgCdTe, InSb, and the like.

Figure 2:
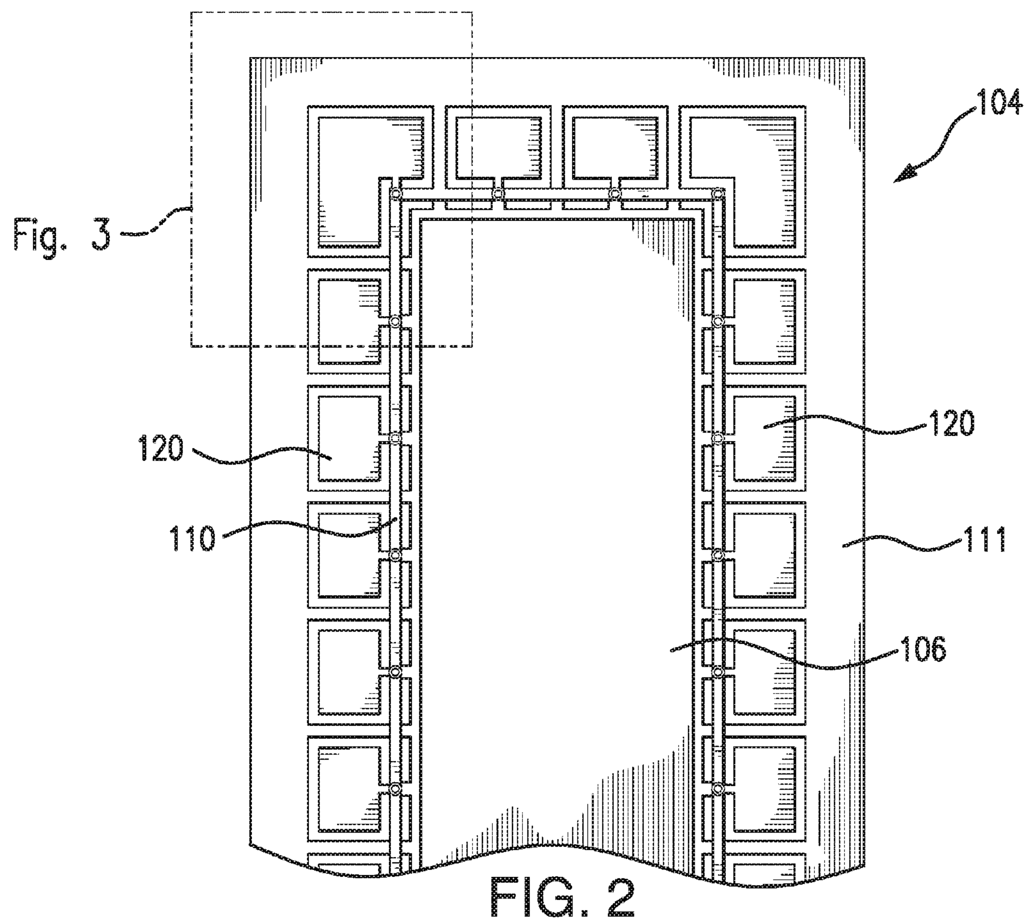
FIG. 2 is a schematic plan view of an exemplary embodiment of a portion of a tunable filter assembly constructed in accordance with the present disclosure, showing a top mirror.
Figure 3:
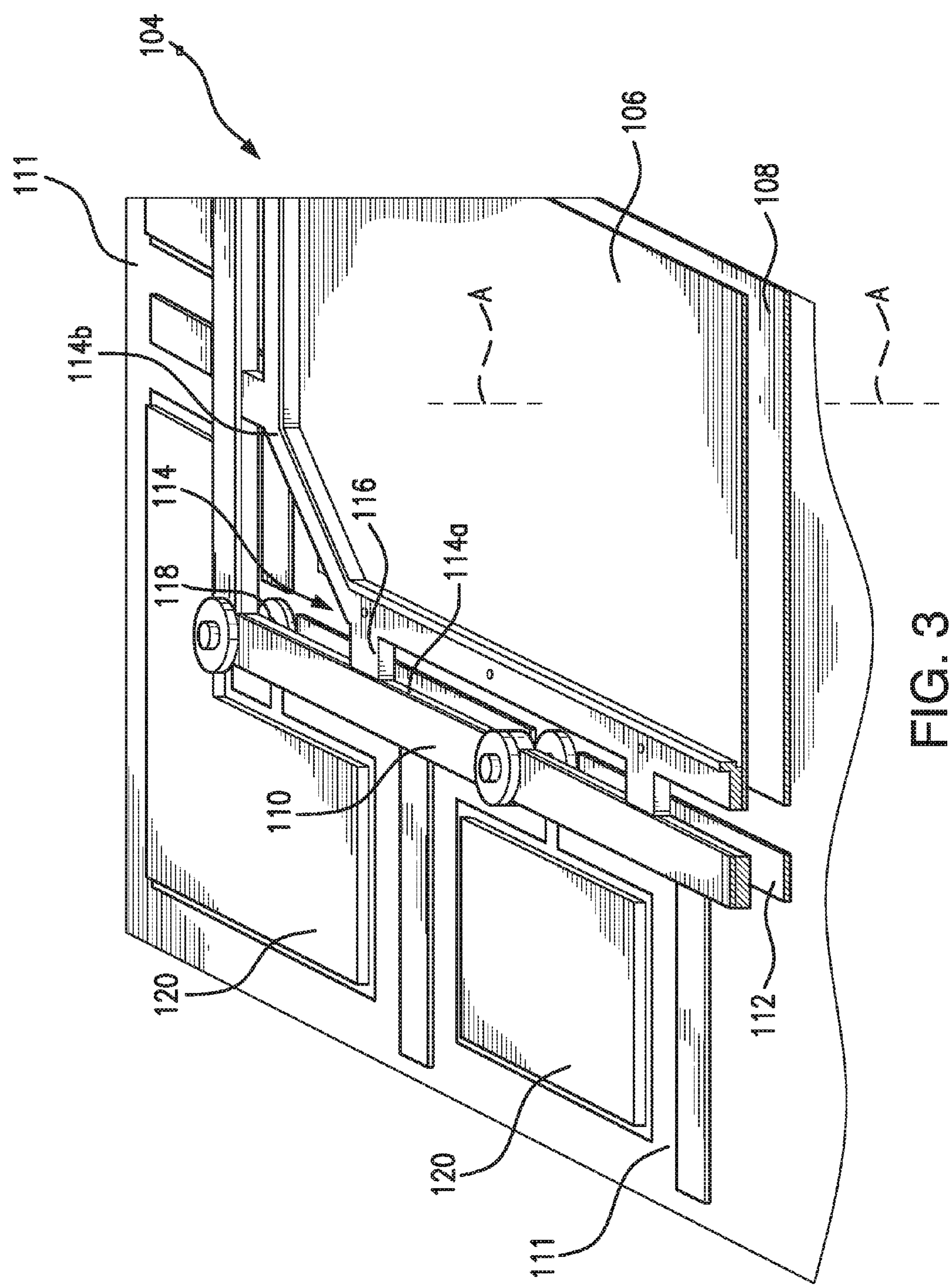
FIG. 3 is a schematic cross-sectional perspective view of a portion of the tunable filter assembly of FIG. 2, showing first and second mirrors, with the first mirror suspended over the second mirror.

With reference now to FIGS. 2 and 3, filter assembly 104 includes a first mirror 106 defining an optical axis A and a second mirror 108 spaced apart from first mirror 106 along optical axis A. First and second mirrors, 106 and 108, respectively face one another. A first electrode 110 is mechanically connected to first mirror 106. A second electrode 112 is fixed relative to second mirror 108. Second mirror 108 and second electrode 112 are both operatively connected to a substrate 111. First and second electrodes 110 and 112, respectively, are positioned relative to one another to adjust the position of first mirror 106 with respect to second mirror 108. The position of first mirror 106 along optical axis A is adjusted by applying a voltage across first and second electrodes 110 and 112, respectively. This adjustment capability allows the bandwidth passing through filter assembly 104 to be tuned as needed, described in further detail below.

With continued reference to FIGS. 2 and 3, tunable filter assembly 104 includes a plurality of electrical bond pads 120 spaced apart along substrate 111 electrically connected to first electrode 110 to supply an even voltage to first electrode 110. The adjustable bandwidth of tunable filter assembly 104 can be within at least one of a short-wave infrared (SWIR), near-infrared (NIR), mid-wave infrared (MWIR), long-wave infrared (LWIR), or visible wave band.

As shown in FIG. 3, a frame 114 is operatively connected between first mirror 106 and first electrode 110 to suspend first mirror 106 over second mirror 108. First electrode 110 is connected to the top of a first portion **114*a* of frame 114 to provide deflection to first portion 114*a* of frame 114 in a direction parallel to optical axis A when a voltage is applied. First mirror 106 is connected to a second portion 114*b* of frame 114. Frame 114 includes a plurality of spaced apart bridges 116 connecting between first and second portions, 114*a* and 114*b*, respectively, of frame 114. A plurality of spaced apart posts 118 extend between first and second electrodes 110 and 112, respectively, to separate first electrode 110 apart from second electrode 112 in a direction parallel to optical axis A. Posts 118 are positioned to allow flexure of first electrode 110 in a direction parallel to optical axis A when a voltage is applied. Each of bridges 116 connect between the first and second portions, 114*a* and 114*b*, respectively, of frame 114 midway between a pair of posts 118 to suspend first mirror 106 and the second portion of frame 114 over second mirror 108**.

Applying a voltage across electrodes 112 and 110 draws first electrode 110 and first portion **114*a* of frame 114 down along optical axis A. Posts 118 keep respective portions of electrode 110 and first portion 114*a* of frame fixed along optical axis A, while the portions in between posts 118 are able to flex. Posts 118 are evenly spaced apart and second portion 114*b* of frame is connected to first portion 114*a* by bridges 116 midway between respective posts 118. The position of bridges 116 is able to maximize the deflection of first electrode 110 and maintain the flatness of first mirror 106. By connecting first portion 114*a* to second portion 114*b* midway between respective posts 118, when first electrode 110 and first portion 114*a* are drawn toward second electrode 112, second portion 114*b* and first mirror 106 are evenly drawn toward second mirror 108 along optical axis A so that the plane of the first mirror 106 remains parallel with the plane of second mirror 108**.

By changing the distance between first and second mirrors 106 and 108, respectively, the spectral transmission permitted to pass through filter assembly 104 to array of pixels 102 is also changed. The closer together first and second mirrors 106 and 108, respectively, are, the shorter the wavelength being transmitted in a given wavelength band will be. The voltage applied can be adjusted in real time to move first mirror 106 along optical axis A as needed for a given application. For example, in a pixel array having a wavelength band ranging from 3.3 microns to 4.3 microns (a MWIR band), filter assembly 104 can be used to adjustably transmit a narrower band ranging from 0.1 microns to 0.5 microns anywhere within the larger MWIR wavelength band. The specific wavelength band being passed will depend on the voltage applied to the electrodes.

Those skilled in the art will readily appreciate that determining the appropriate wavelength bands for a given application can be done by a variety of methods. For example, one method for selecting narrower wavelength bands within the larger focal plane wavelength band includes choosing a target signature and determining the conditions around the target (e.g. sand, smoke, etc.). The conditions around the target are compared to pre-determined data or real-time data to determine the wavelength bands appropriate for that target signature under those particular conditions. The method includes modifying voltages applied to pairs of electrodes to alter the distance between mirrors of filters, e.g. filter assembly 104, to change the transmissible wavelength bands to correspond to the wavelength bands determined to be appropriate for that particular target at that condition. The systems and methods described herein combine benefits of multispectral and hyperspectral imaging and provide long range spectral discrimination of targets of interest. Additionally, the increased spectral diversity will reduce the amount of data and processing required to identify the target material.

The methods and systems of the present disclosure, as described above and shown in the drawings provide for optical sensors with superior properties including improved imaging quality. While the apparatus and methods of the subject disclosure have been shown and described with reference to preferred embodiments, those skilled in the art will readily appreciate that changes and/or modifications may be made thereto without departing from the spirit and scope of the subject disclosure.

What is claimed is:

1. An optical sensor comprising:

an array of pixels configured to convert photons into electrons for forming an image; and a tunable filter assembly optically connected to the array of pixels for passing an adjustable bandwidth of photons to the array of pixels, wherein the tunable filter assembly includes:

a first mirror defining an optical axis;

a second mirror spaced apart from the first mirror along the optical axis; and a first electrode mechanically connects to the first mirror; and a second electrode fixed relative to the second mirror, wherein the first and second electrodes are positioned relative to one another to adjust the position of the first mirror with respect to the second mirror when a voltage is applied across the first and second electrodes to tune the spectral bands being passed through the filter assembly to the array of pixels.

2. An optical sensor as recited in claim 1, wherein the tunable filter assembly is one of a plurality of filter assemblies arranged in rows over the array of pixels, wherein each filter assembly is optically connected to respective sections of the array of pixels to pass a separate adjustable bandwidth to one of the respective sections to create high-resolution, long-range multi-spectral imagery with tunable spectral bands.

3. An optical sensor as recited in claim 1, wherein the tunable filter assembly is one of three filter assemblies arranged in rows over the array of pixels, wherein each filter assembly is optically connected to respective sections of the array of pixels to pass a separate adjustable bandwidth to one of the respective sections to create high-resolution, long-range multi-spectral imagery with tunable spectral bands.

4. An optical sensor as recited in claim 1, wherein the tunable filter assembly includes a plurality of electrical bond pads spaced apart along the array of pixels electrically connected to the first electrode to supply an even voltage to the first electrode.

5. An optical sensor as recited in claim 1, wherein the adjustable bandwidth of the tunable filter assembly is within at least one of a SWIR, NIR, MWIR, LWIR, or visible band.

6. An optical sensor as recited in claim 1, wherein the tunable filter assembly includes a frame operatively connected between the first mirror and the first electrode, wherein the first electrode is connected to a first portion of the frame and the first mirror is connected to a second portion of the frame, wherein the frame includes a plurality of spaced apart bridges connecting between the first and second portions of the frame to suspend the first mirror and the second portion of the frame over the second mirror.

7. An optical sensor as recited in claim 6, wherein the tunable filter assembly includes a plurality of spaced apart posts extending between the first and second electrodes to separate the first electrode apart from the second electrode in a direction parallel to the optical axis.

8. An optical sensor as recited in claim 7, wherein each of the bridges of the frame connect between the first and second portions of the frame midway between a respective pair of the posts.

9. An optical sensor as recited in claim 8, wherein the posts are positioned to allow flexure of the first electrode and the first portion of the frame in a direction parallel to the optical axis when a voltage is applied, thereby adjusting the position of the first mirror along the optical axis and tuning the adjustable bandwidth passing through the tunable filter assembly.

10. An optical sensor as recited in claim 1, wherein the array of pixels and the tunable filter assembly are cryogenically cooled.

* * * * *